United States Patent [19]

Obermeier et al.

[11] Patent Number: 4,601,852
[45] Date of Patent: Jul. 22, 1986

[54] PROCESS FOR THE PREPARATION OF HUMAN OR THE DERIVATIVES THEREOF FROM PIG INSULIN OR THE DERIVATIVES THEREOF

[75] Inventors: Rainer Obermeier, Hattersheim am Main; Jürgen Ludwig, Brachttal; Gerhard Seipke, Wiesbaden, all of Fed. Rep. of Germany

[73] Assignee: Hoechst Aktiengesellschaft, Frankfurt am Main, Fed. Rep. of Germany

[21] Appl. No.: 641,357

[22] Filed: Aug. 15, 1984

Related U.S. Application Data

[63] Continuation of Ser. No. 339,731, Jan. 15, 1982, abandoned.

[30] Foreign Application Priority Data

Jan. 17, 1981 [DE] Fed. Rep. of Germany ....... 3101382

[51] Int. Cl.$^4$ .............................................. C07K 7/40
[52] U.S. Cl. ................................................... 530/303
[58] Field of Search ..................................... 260/112.7

[56] References Cited

U.S. PATENT DOCUMENTS

| 3,276,961 | 10/1966 | Bodanszky et al. | 260/112.7 |
| 3,903,068 | 9/1975 | Ruttenberg | 260/112.7 |
| 4,029,642 | 6/1977 | Obermeier | 260/112.7 |

FOREIGN PATENT DOCUMENTS

| 574/80 | 8/1981 | Denmark | 260/112.7 |
| 540/81 | 8/1981 | Denmark | 260/112.7 |
| 17938 | 10/1980 | European Pat. Off. | 260/112.7 |
| 45187 | 2/1982 | European Pat. Off. | 260/112.7 |
| 2460753 | 6/1976 | Fed. Rep. of Germany | 260/112.7 |
| 2069502 | 8/1981 | United Kingdom | 260/112.7 |

OTHER PUBLICATIONS

Morihara et al., Nature 280, 412, 413 (1979).
Morihara et al., Chem. Abstr. 92, 142752 (1980).
Morihara et al., Biochem. Biophys. Res. Comm. 92, 396–402 (1980).
Chem. Abstr., 9th Collective Index, vols. 76–85 (1972–1976), p. 5608 GS.
Hennrich, Kontakte 1/73, pp. 8–11, E. Merck, Darmstadt, (1973).
Hennrich, Kontakte 2/73, pp. 3–8, E. Merck, Darmstadt, (1973).
Young et al., J. Biol. Chem. 236, 743–748 (1961).
Jonczyk et al., Z. Physiol. Chemie 362, 1591–1598 (1981).
Rose et al., "Rapid Preparation of Human Insulin and Insulin Analogues in High Yield by Enzyme–Assisted Semi-Synthesis", Biochem. J., (1983) 211, 671–676.
Jonczyk et al., "Eine neue Semisynthese des Humaninsulins Tryptisch-Katalysierte Transpeptidierung von Schweineinsulin mit L-Threonon-tert-butylester", Z. Physical. Chem., 362, 1591–1598 (1981).
"Basic Principles of Organic Chemistry", Roberts et al., W. A. Benjamin, Inc., New York, 1965, pp. 715–716.
"Biochemistry", Lehninger, Worth Publishers, Inc., New York, 1970, pp. 158–159.
Fruton, "Proteinase–Catalyzed Synthesis of Peptide Bonds", Advances in Enzymology 53, 239–306, Ed. A. Mesiter, J. Wily & Sons (1982), pp. 256–258.

*Primary Examiner*—Frederick E. Waddell
*Attorney, Agent, or Firm*—Curtis, Morris & Safford

[57] ABSTRACT

What is disclosed is a method for making human insulin or modified human insulin from pig insulin or modified pig insulin by reacting the pig insulin starting material at a pH below its isoelectric point with an excess of a threonine ester in the presence of trypsin or a trypsin-like enzyme.

16 Claims, No Drawings

PROCESS FOR THE PREPARATION OF HUMAN OR THE DERIVATIVES THEREOF FROM PIG INSULIN OR THE DERIVATIVES THEREOF

This application is a continuation of application Ser. No. 339,731, filed Jan. 15, 1982, now abandoned.

Human insulin and pig insulin differ due to the carboxyl-terminal amino acid in B30-position of the insulin B chain. In the case of human insulin, a threonine follows the lysyl radical in B29, while in the case of pig insulin alanine comes thereafter.

In addition to the total synthesis of human insulin [Märkli et al., Hoppe-Seyler's Z. Physiol. Chem. 360, 1699–1632 (1979)], various semisynthetic processes allow the replacement of alanine by threonine in pig insulin as starting material.

For the manufacture of larger amounts of human insulin, total synthesis is too expensive.

In the semi-synthesis process of Ruttenberg (U.S. Pat. No. 3,903,068) and Obermeier and Geiger [R. Obermeier et al., Hoppe-Seyler's Z. Physiol. Chem. 357, 759–767 (1976)], a desoctapeptide-B23–30 pig insulin obtained by tryptic digestion is linked according to peptide-chemical methods to a protected, synthetic octapeptide of the human insulin sequence B23–30. After all protective groups are split off, complicated purification steps are carried out. The yields of human insulin are poor.

Higher yields in the conversion of natural pig insulin to human insulin are obtained by enzymatic processes. Inouye et al., J. Am. Chem. Soc. 101, 751–752 (1979) have developed a process according to which desoctapeptide-B23–30 pig insulin is converted to human insulin by means of synthetic octapeptide-B23–30 (human) with tryptic catalysis. Disadvantageous in this reaction is the use of a synthetic octapeptide which, as in the cases of Ruttenberg and Obermeier, has to be prepared with considerable expenditure.

The conversion is more economic when the last amino acid B30 only of pig insulin has to be replaced. In U.S. Pat. No. 3,276,961, Bodanszky et al. describe a process in which human insulin is prepared from animal insulins with the aid of enzymes such as tyrpsin and carboxypeptidase A in the presence of threonine. However, the process cannot be carried out because, under the conditions described, not only Lys-Ala (B29–30), but also other peptide bonds in the insulin are split.

H. G. Gattner et al., Insulin, ed. D. Brandenburg, A. Wollmer, 1980, Proc. 2nd. Intern. Insulin Symposium 1979, pp. 118–123, or K. Morihara et al., Nature 280, 412–413 (1979), as well as EP-A No. 0017938 start from Des-Ala-B30 insulin (pig) and in a two-step process link it with threonine-methyl ester or threonine-tert.-butyl ester by means of trypsin to form the corresponding human insulin ester. After the ester group is split off by treatment with sodium hydroxide solution or trifluoroacetic acid, human insulin is obtained with good yields.

The two last-mentioned processes use Des-Ala-B30 pig insulin as starting material, which is obtained from pig insulin by means of carboxypeptidase A (CPA). CPA splits stepwise carboxyl-positioned neutral and acidic L-amino acids of peptides and proteins. The amino acids are split off with differing splitting kinetics. In the case of basic amino acids, the enzymatic degradation stops at lysine-B29 or arginine-B22 of the insulin-B chain. Thus, the alanine radical in B30-position of the insulin-B chain can be eliminated without the chain degradation processing further.

The disadvantage of CPA digestion, however, resides in the simultaneous attack of the enzyme on the C-terminal amino acid asparagine in A21-position of the insulin-A chain. Under the general digestion conditions of CPA, about 10–20% of asparagine and, simultaneously, 80–90% of alanine are eliminated from pig insulin due to the differing cleavage speed. Therefore, such a digestion product contains a mixture of Des-Ala-B30-des-Asn-A21, Des-Ala-B30 and Des-Asn-A21 insulin in addition to unreacted insulin.

E. W. Schmitt et al., Hoppe-Seyler's Z. Physiol.-Chem. 359, 799–802 (1978) succeeded in reducing the formation of Des-Ala-B30-des-Asn-A21 insulin to less than 5 to 10% by using $NH_4^+$-containing buffers. Despite column chromatography purification, however, it cannot be excluded that a human insulin so prepared still causes distinct immunological reactions.

A semisynthetic process has now been found which allows the conversion of pig insulin to human insulin ester with the aid of trypsin in one single step while avoiding CPA digestion. From the ester, human insulin can be obtained in the usual manner. The total yield of the one-step reaction is 50 to 65%. In addition to the considerably simplified reaction operations, the advantage of the process resides in obtaining human insulin which cannot contain any of the above impurities and is thus suitable for administration even in immunological problem cases.

The subject of the invention is therefore a process for the preparation of human insulin or the derivatives thereof from pig insulin or the derivatives thereof, which comprises reacting pig insulin or a derivative thereof at a pH below its isoelectric point with an excess of a threonine ester or one of its derivatives containing a free amino group in the presence of trypsin or a trypsin-like enzyme.

Suitable starting materials for the reaction according to the invention are original pig insulin and the derivatives thereof which can be obtained by incorporation of protective groups at free functions or by splitting-off or replacement of individual amino acids. When using such derivatives of pig insulin, a human insulin is obtained which contains the corresponding protective groups or sequences. A preferred derivative of pig insulin to be subjected to the reaction of the invention is Des-Phe$^{B1}$ pig insulin which is converted to the corresponding Des-Phe$^{B1}$ human insulin.

Further preferred derivatives of pig insulin are those carrying a protective group in $N^{\alpha B1}$-position. Preferred protective groups in this position are especially the t-butyloxycarbonyl-(BOC) or dimethoxyphenylpropyloxycarbonyl-(DDZ-) radical. Other protective groups are known from E. Wünsch, Methoden der organischen Chemie (Houben-Weyl), Vol. XV/1, Stuttgart 1974.

In accordance with the invention, the reaction is carried out at a pH below the isoelectric point of the starting insulin or insulin derivative. The isoelectric point of pig insulin is at pH 5.4, and it is therefore recommended to operate at a pH below 5.4 when using pig insulin as a starting material. On the other hand, limits are set to operations at a low pH because of the stability of the insulin and because of the enzyme activity in a strongly acidic medium. The reaction should therefore be carried out at a pH in the range of from 4 to 6.

It has proved to be advantageous to react the insulin or insulin derivative with a threonine ester acetate in an aqueous medium which had been adjusted to a weakly acidic pH of about 5 by means of a weak organic acid, preferably acetic acid. The advantage of this special process variant resides above all in an increased yield as compared to operations in aqueous organic solvents. Further advantages are savings of organic solvent and easier work-up of the reaction mixture, because there is no separation of organic solvent.

The reaction may be carried out at room temperature; slight warming, however, is recommended in order to accelerate its course. On the other hand, a temperature of 40° C. should not be exceeded; operations while cooling do not bring about any advantages, either.

Alternatively to trypsin, such enzymes are suitable for the process of the invention which are known from the literature to be similar to trypsin, that is, those which split specific peptide bonds at the terminal carboxyl of basic amino acids. The amount of enzyme used is not critical, and the weight ratio of pig insulin to enzyme may be in a range of from 1:1 to 100:1. Preferred, however, is a weight ratio of about 10:1.

Suitable threonine esters are all known L-threonine esters, for example L-threonine-tert.-butyl ester, L-threonine-O.tert.-butyl-tert.-butyl ester or L-threonine-methyl ester. By derivatives of threonine esters in accordance with the invention there are to be understood those which carry a protective group, especially the ether protective group, at the OH function of threonine.

As compared to the insulin, the threonine ester must be used in an excess of about 10- to 100-fold the molar amount of insulin.

The reaction of the invention gives first B30 esters of human insulin which, if desired, can be converted to free human insulin by splitting off the ester group according to known methods.

Before conversion to free insulin, it is advantageous to subject the ester to the required purification operations, for example according to column chromatography methods.

In usual administration formulations, the insulin so obtained can be used as medicament for the treatment of diabetes mellitus.

The following examples illustrate the invention.

EXAMPLE 1

120 mg of pig insulin and 231 mg of Tr-(O-tBu)-tBu were suspended in 2 ml of 0.1 molar pyridine-acetate buffer having a pH of 4.0 and dissolved by adding 3 ml of DMF. The pH of the solution was examined and optionally adjusted anew to 4.0 by means of acetic acid or pyridine. 5 mg of TPCK-trypsin were added at 30° C. to the transparent solution. In intervals of 4 hours each, two further portions of 5 mg of TPCK-trypsin were added. The reaction medium was then agitated for 16 hours at 35° C. The solution was then acidified to pH 2–3 by means of 1N HCl, and precipitated by adding 1 ml of ethanol and 5 ml of ether. The precipitate was centrifuged off and triturated with ether. The pulverulent residue was then purified as described in Obermeier et al. by distribution chromatography on Sephadex ® LH20. The fractions containing the human insulin ester so separated were concentrated in vacuo at room temperature, and precipitated with acetone/ether. Pig insulin unreacted and recovered can be reused for the semi-synthesis. The precipitate formed was centrifuged off and dried. Yield: 81 mg.

For splitting off the protective groups, the product was dissolved in 3 ml of 6N HCl saturated with anisol while heating for a short time to 40° C. Subsequently, it was cooled and adjusted at 0° C. to pH 2–3 by means of 10% sodium hydroxide solution. By adding 30 ml of acetone, the human insulin was precipitated. The precipitate was centrifuged off and dried under reduced pressure. Yield: 77 g of human insulin.

In the blood sugar lowering test on rabbits, the human insulin so obtained showed full biological activity of 26 I.U./mg, relative to pig insulin.

The amino acid analysis corresponding to the theoretical values for human insulin:

|     | theory | found |
| --- | --- | --- |
| Glu | 7 | 7.00 |
| Ala | 1 | 1.04 |
| Thr | 3 | 2.88 |
| Lys | 1 | 1.01 |

EXAMPLE 2

120 mg of pig insulin and 133 mg of threonine-methyl ester were converted according to Example 1 to human insulin ester, and purified. The product so obtained (73 mg) was stirred for 15 minutes at 0° C. with 0.1 ml of 0.1N NaOH. Subsequently, it was neutralized with 0.5 ml of 0.1N HCl, dialyzed and lyophilized. The human insulin (68 mg) so formed had full biological activity, and the amino acid analysis corresponded to the theoretical values.

EXAMPLE 3

120 mg of pig insulin and 175 mg of threonine-tert.-butyl ester were reacted according to Example 1, and purified. Yield: 76 mg of human insulin-tert.-butyl ester. The product was dissolved in 1 ml of trifluoroacetic acid and 0.05 ml of anisol, and stirred for 60 minutes at room temperature. The unprotected human insulin so formed was precipitated by addition of 8 ml of ether, and centrifuged off. The residue was dissolved in water, dialyzed and lyophilized. Yield: 71 mg of human insulin having full biological activity and a correct amino acid composition.

EXAMPLE 4

115 mg of Des-Phe$^{B}$1 pig insulin were reacted according to Example 1 with 231 mg of Thr-(tBu)-O-tBu and purified. Yield: 75 mg of Des-Phe$^{B}$1 human insulin-B30-di-tert.-butyl ester. After the tert.-butyl groups are split off and after isolation according to Example 1, 70 mg of free Des-Phe$^{B}$1 human insulin was obtained.

Biological activity: 26 I.U./mg
Amino acid analysis:

|     | theory | found |
| --- | --- | --- |
| Glu | 7 | 7.00 |
| Ala | 1 | 0.98 |
| Thr | 3 | 2.90 |
| Phe | 2 | 2.10 |
| Lys | 1 | 1.03 |

EXAMPLE 5

120 mg of pig insulin were reacted with 231 mg of Thr-(tBu)-O-tBu according to Example 1. Instead of trypsin, 0.50 ml of trypsin bound to agarose gel were used. After the trypsin agarose is filtered off, the solution was worked up as indicated in Example 1. Yield of human insulin: 61 mg.

EXAMPLE 6

5 g of pig insulin and 30 g of Thr-(tBu)-O-tBu-acetate were dissolved in 20 ml of water and adjusted to pH 5.0–5.2 by means of acetic acid. For dissolving the reactants, 400 mg of trypsin dissolved in 2 ml of water were added. The course of the reaction was supervised by means of acetate film electrophoresis. After maximal conversion (about 90%) of the pig insulin used, the crude reaction product was precipitated by addition of 200 ml of methanol and 50 ml of di-isopropyl ether. After centrifugation and drying, the yield is 5.1 g of raw material, which after HPCl analysis contained 90% of human insulin-B30-tBu$_2$.

EXAMPLE 7

In 30 ml of aqueous 37.5% acetic acid, 5 g of N$^{\alpha B1}$-BOC-pig insulin and 24 g of Thr(tBu)OtBu were dissolved one after the other and 400 mg of trypsin in 2 ml of water were added as indicated in Example 6. The reaction proceeded as in Example 6 and was stopped after maximal conversion by precipitation with methanol/di-isopropyl ether. After isolation and drying, the yield was 5.0 g of raw material which according to HPCl analysis contained 87% of N$^{\alpha B1}$-BOC-human insulin-B30-tBu$_2$.

EXAMPLE 8

10 g of pig insulin were dissolved in 45 ml of water with addition of 5 ml of acetic acid. 33 g of Thr(tBu)-O-tBu-acetate were added to the insulin solution and 0.8 g of trypsin, dissolved in 5 ml of water, was stirred into the transparent solution. After 16 hours at room temperature, the reaction was interrupted by precipitation of the reaction mixture with the use of a mixture of methanol/di-isopropanol (500 ml, 4:1=v/v), and work-up was as indicated in Example 1. Yield of human insulin ester: 4.0 g.

EXAMPLE 9

10 g of pig insulin were dissolved in 40 ml of water with addition of 5 ml of acetic acid together with 60 g of Thr(tBu)-O-tBu-acetate. 0.8 g of trypsin dissolved in 2 ml of water were added to the mixture of reactants. The reaction was interrupted after 16 hours at room temperature as indicated in Example 8 and the reaction mixture was worked up. Yield after purification: 4.1 g of human insulin ester.

EXAMPLE 10

120 mg of pig insulin were dissolved in 0.5 ml of water and 0.04 ml of acetic acid together with 380 mg of Thr(tBu)-O-tBu-acetate. 10 units of lysylendopeptidase-Lys-Cl (5 mg of protein) were added to the solution. After 16 hours at room temperature, the reaction mixture was worked up as in Example 8, and purified. Yield of human insulin ester: 61 mg.

EXAMPLE 11

1.35 kg of Thr(tBu)-O-tBu were dissolved in 1 l of petroleum ether, and cooled with ice. 340 ml of acetic acid were stirred into the solution and this solution was cooled at 0° C. until crystallization was complete. The crystallized Thr(tBu)-O-tBu-acetate was filtered off, washed with petroleum ether (0° C.), and dried in vacuo. Yield of Thr(tBu)-O-tBu-acetate: 1.44 kg (m.p. 58°–60° C.).

What is claimed is:

1. A method for making a product which is human insulin having free functional groups or having one or more protected functional groups, which method comprises reacting a pig insulin reagent which is pig insulin having free functional groups or having one or more protected functional groups, in water at a temperature not exceeding 40° C. and at a pH between pH 4 and the isoelectric point of said pig insulin reagent, the pH value being adjusted by the addition of a weak organic acid, and in the presence of a trypsin or of a trypsin-like enzyme, the weight ratio of insulin to enzyme being in the range from 1:1 to 100:1, with L-threonine-di-tert.-butyl ester acetate, which is used in an about 10-fold to 100-fold molar excess with respect to insulin, and then removing said tert.-butyl group from the product so obtained.

2. A method for making a product which is human insulin having free functional groups or having one or more protected functional groups, or is such human insulin wherein at least one individual amino acid has been replaced by another amino acid, or is des-Phe$^{B1}$ human insulin, which method comprises reacting a pig insulin reagent which is pig insulin having free functional groups or having one or more protected functional groups, or is such pig insulin wherein at least one individual amino acid thereof has been replaced by another amino acid, or is des-Phe$^{B1}$ pig insulin, in water or in an aqueous medium containing an organic solvent, at a pH below the isoelectric point of said pig insulin reagent, and in the presence of trypsin or of a trypsin-like enzyme, with an excess of an L-threonine-(C$_1$-C$_4$)alkyl ester having a free or ether-protected OH-function, and then removing said (C$_1$-C$_4$)alkyl group from the product so obtained.

3. A method as in claim 2 wherein said pig insulin reagent has one or more protected functional groups and wherein groups protective of said functional groups are removed subsequent to the reaction.

4. A method as in claim 2 wherein said L-threonine-(C$_1$-C$_4$)alkyl ester is Thr(Bu$^t$)OBu$^t$.

5. A method as in claim 2 where the content of water in said aqueous medium is more than 50 percent (vol.-/vol.).

6. A method as in claim 2 wherein the pH value is adjusted by the addition of a weak organic acid.

7. A method as in claim 6 where in the weak organic acid is acetic acid.

8. A method as in claim 2 wherein said threonine-(C$_1$-C$_4$)-alkyl ester is di-tert.-butyl-threonine acetate.

9. A method as in claim 2 wherein the reaction is carried out at a temperature not exceeding 40° C.

10. A method as in claim 2 wherein said threonine ester is used in a 10-fold to 100-fold molar excess with respect to insulin.

11. A method as in claim 2 wherein the weight ratio of pig insulin to enzyme is in the range from 1:1 to 100:1.

12. A method as in claim 2 wherein said pig insulin reagent and said ester are reacted in the absence of an organic solvent.

13. A method as in claim 2 wherein Des-Phe$^{B1}$ human insulin is prepared from Des-Phe$^{B1}$ pig insulin.

14. A method as in claim 2 wherein said pig insulin reagent and ester are reacted at a pH between pH 4 and the isoelectric point.

15. A method as in claim 2 wherein said pig insulin reagent has a protected functional group in the $N_\alpha^{B1}$-position.

16. A method as in claim 15 wherein said $N_\alpha^{B1}$-functional group is protected by t-butyloxycarbonyl or dimethoxyphenyl-propyloxycarbonyl.

* * * * *

UNITED STATES PATENT AND TRADEMARK OFFICE
CERTIFICATE OF CORRECTION

PATENT NO. : 4,601,852

DATED : July 22, 1986

INVENTOR(S) : Obermeier et al.

It is certified that error appears in the above-identified patent and that said Letters Patent is hereby corrected as shown below:

Correct the title in the patent from:

"PROCESS FOR THE PREPARATION OF HUMAN OR THE DERIVATIVES THEREOF FROM PIG INSULIN OR THE DERIVATIVES THEREOF" to

--PROCESS FOR THE PREPARATION OF HUMAN INSULIN OR THE DERIVATIVES THEREOF FROM PIG INSULIN OR THE DERIVATIVES THEREOF--

Signed and Sealed this

Thirteenth Day of January, 1987

Attest:

DONALD J. QUIGG

Attesting Officer

Commissioner of Patents and Trademarks